United States Patent
Yamada

(10) Patent No.: US 8,574,175 B2
(45) Date of Patent: *Nov. 5, 2013

(54) TREATMENT APPARATUS AND OPERATION SYSTEM

(75) Inventor: Norihiro Yamada, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/418,555

(22) Filed: Mar. 13, 2012

(65) Prior Publication Data

US 2012/0172766 A1   Jul. 5, 2012

Related U.S. Application Data

(63) Continuation of application No. PCT/JP2009/066855, filed on Sep. 18, 2009.

(51) Int. Cl.
*A61H 1/00* (2006.01)

(52) U.S. Cl.
USPC .......................................................... 601/3

(58) Field of Classification Search
USPC .......................................................... 601/3
See application file for complete search history.

(56) References Cited

U.S. PATENT DOCUMENTS

| | | | |
|---|---|---|---|
| 5,195,959 A * | 3/1993 | Smith | 604/34 |
| 5,235,524 A * | 8/1993 | Barkhoudarian | 702/39 |
| 5,484,398 A | 1/1996 | Stoddard | |
| 6,497,140 B1 | 12/2002 | Zeqiri | |
| 2002/0194907 A1* | 12/2002 | Bostrom et al. | 73/152.58 |
| 2003/0018256 A1* | 1/2003 | Sasaki et al. | 600/439 |
| 2005/0234446 A1* | 10/2005 | Van Wyk et al. | 606/41 |
| 2006/0253050 A1 | 11/2006 | Yoshimine et al. | |
| 2008/0058803 A1 | 3/2008 | Kimura | |
| 2008/0194999 A1* | 8/2008 | Yamaha et al. | 601/2 |

FOREIGN PATENT DOCUMENTS

| | | |
|---|---|---|
| EP | 1 790 303 A | 5/2007 |
| EP | 1 894 532 A1 | 3/2008 |
| JP | 2001-133321 | 5/2001 |
| JP | 2008-055151 | 3/2008 |
| JP | 2008-188160 | 8/2008 |
| JP | 2008-194457 | 8/2008 |
| WO | WO 2006/030563 A1 | 3/2006 |

OTHER PUBLICATIONS

International Search Report dated Nov. 2, 2009 issued in PCT/JP2009/066855.

* cited by examiner

*Primary Examiner* — Tse Chen
*Assistant Examiner* — Hien Nguyen
(74) *Attorney, Agent, or Firm* — Scully, Scott, Murphy & Presser, P.C.

(57) ABSTRACT

A treatment apparatus of the present invention includes a cavitation generation section that generates cavitations at a treatment target region of a treatment subject; a detection section that detects cavitations that are generated at the treatment target region; and a control section that controls a generation state of cavitations at the treatment target region by controlling a physico-chemical parameter of the treatment target region based on a detection result at the detection section.

6 Claims, 5 Drawing Sheets

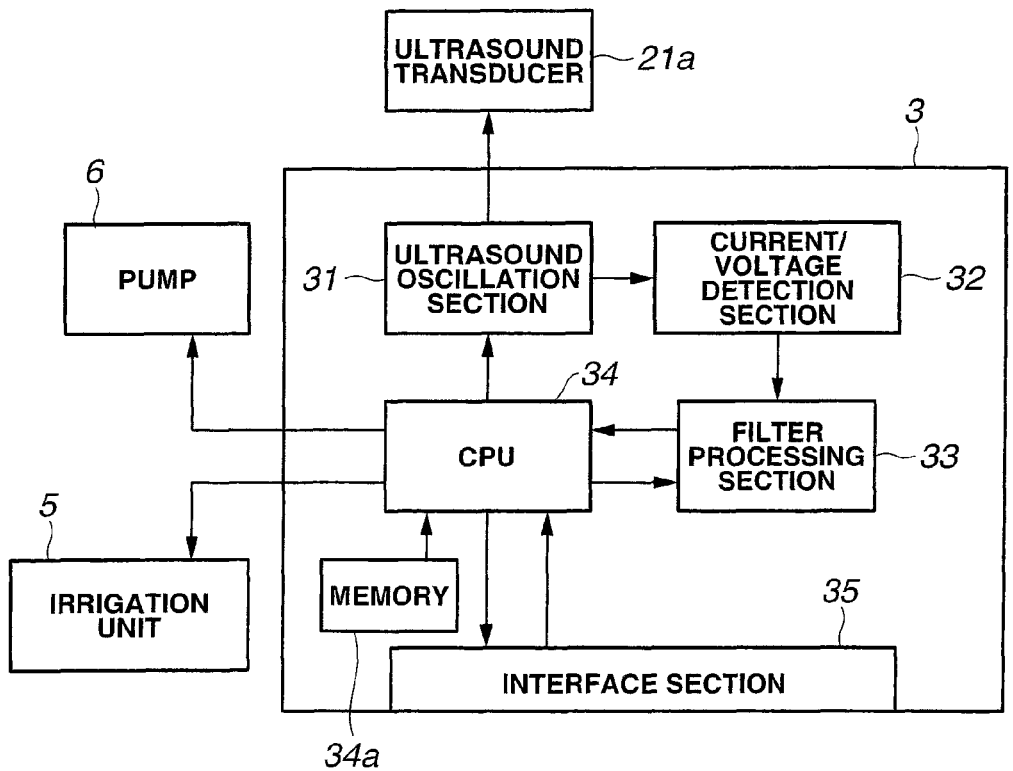
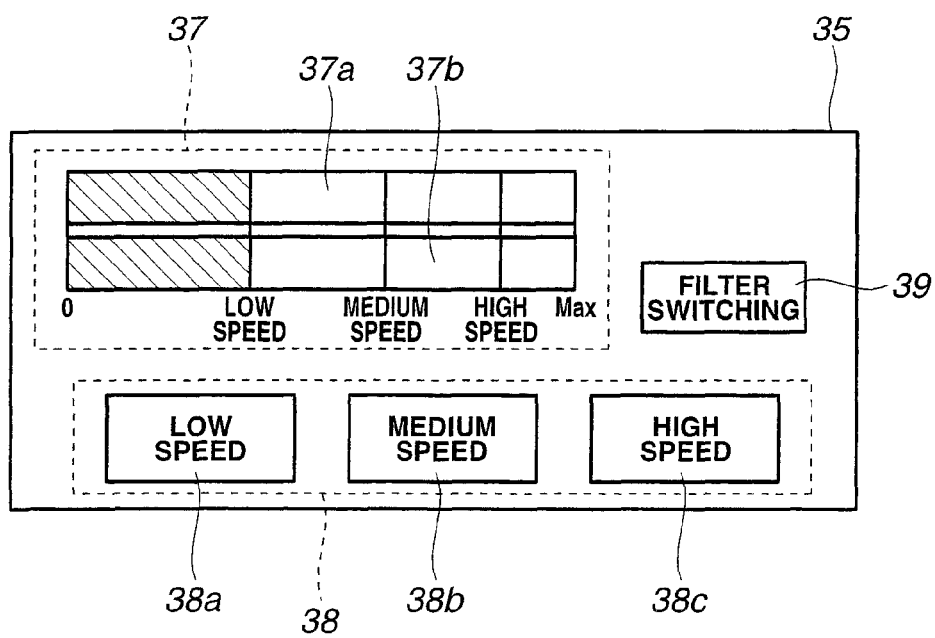

TREATMENT APPARATUS AND OPERATION SYSTEM

CROSS REFERENCE TO RELATED APPLICATION

This application is a continuation application of PCT/JP2009/066855 filed on Sep. 18, 2009, the entire contents of which are incorporated herein by this reference.

BACKGROUND OF THE INVENTION

1. Field of the Invention

The present invention relates to a treatment apparatus and an operation system that perform treatment utilizing cavitations.

2. Description of the Related Art

Apparatuses (hereafter, referred to as "ultrasound treatment apparatuses") that perform treatment with respect to living tissue by utilizing ultrasound vibrations or various phenomena that arise accompanying ultrasound vibrations are already widely known. As examples of such kind of apparatus, an ultrasound operation handpiece disclosed in U.S. Pat. No. 5,484,398 and an ultrasound operation device disclosed in Japanese Patent Application Laid-Open Publication No. 2008-188160 may be mentioned.

It is considered that the treatment capability of an ultrasound treatment apparatus depends greatly on the state of cavitation generation at a treatment target region. Therefore, in order to perform treatment efficiently using an ultrasound treatment apparatus, control that causes cavitations being generated at a treatment target region to be generated in an appropriate state in accordance with the contents of a treatment is essential.

SUMMARY OF THE INVENTION

A treatment apparatus of the present invention has a cavitation generation section that generates cavitations at a treatment target region of a treatment subject, a detection section that detects cavitations that are generated at the treatment target region, and a control section that controls a generation state of cavitations at the treatment target region by controlling a physico-chemical parameter of the treatment target region based on a detection result at the detection section.

An operation system in the present invention has an ultrasound transducer that is capable of generating ultrasound vibrations; a drive section that drives the ultrasound transducer by means of a drive signal; a probe that has a proximal end portion that is mechanically connected with the ultrasound transducer, and a distal end portion that can be brought adjacent to or in contact with a treatment target region of a treatment subject, the probe being capable of transmitting ultrasound vibrations generated at the ultrasound transducer from the proximal end portion to the distal end portion; a physico-chemical parameter adjustment section that changes a physico-chemical parameter of the treatment target region; a detection section that detects a physical quantity that changes due to cavitations that are generated at the treatment target region by ultrasound vibrations of the distal end portion, based on the drive signal that is supplied to the ultrasound transducer; and a control section that controls a generation state of cavitations at the treatment target region by controlling the physico-chemical parameter adjustment section based on a detection result of the detection section.

BRIEF DESCRIPTION OF THE DRAWINGS

FIG. 2 is a block diagram that shows an example of the specific configuration of an ultrasound driving power supply shown in FIG. 1;

FIG. 4 is a view that shows an example of the specific configuration of an interface section shown in FIG. 2;

DETAILED DESCRIPTION OF THE PREFERRED EMBODIMENTS

An embodiment of the present invention is described hereunder with reference to the drawings.

Figure 1:
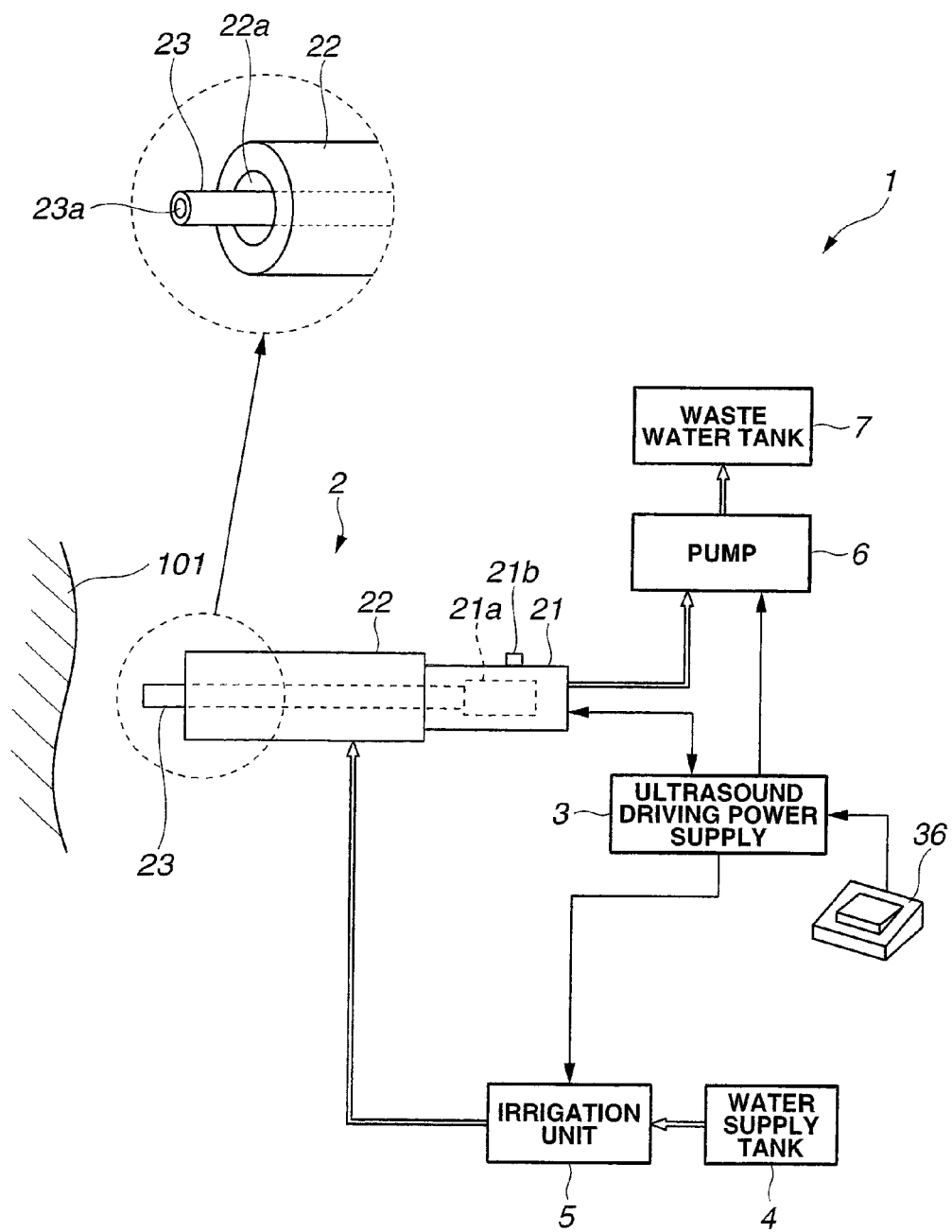
FIG. 1 is a view that shows an example of the configuration of an operation system according to an embodiment of the present invention.

As shown in FIG. 1, an operation system 1 has an ultrasound treatment handpiece 2 that crushes and emulsifies living tissue of a treatment target region 101 by an action of ultrasound vibrations, an ultrasound driving power supply 3 that supplies an ultrasound drive signal for driving the ultrasound treatment handpiece 2, a water supply tank 4 in which physiological saline is stored, an irrigation unit 5 that sucks up physiological saline stored in the water supply tank 4 and supplies the physiological saline to the ultrasound treatment handpiece 2, a pump 6 that sucks living tissue that has been crushed and emulsified by the ultrasound treatment handpiece 2, and a waste water tank 7 in which fluid that has been sucked up by the pump 6 is stored.

The ultrasound treatment handpiece 2 is equipped with a function as a cavitation generation section, and includes a grasping section 21 that is grasped by a surgeon or the like, a sheath 22 that is provided in a linked manner with respect to a distal end side of the grasping section 21, and a probe 23 equipped with a hollow shape and having a distal end portion that protrudes from the distal end side of the sheath 22.

An ultrasound transducer 21a is provided inside the grasping section 21. The ultrasound transducer 21a is equipped with a predetermined resonance frequency and is mechanically connected to the proximal end portion of the probe 23, and generates ultrasound vibrations in accordance with an ultrasound drive signal that is supplied from the ultrasound driving power supply 3. The probe 23 can transmit ultrasound vibrations that are generated by the ultrasound transducer 21a from the proximal end portion of the probe 23 to the distal end portion thereof.

More specifically, ultrasound vibrations generated at the ultrasound transducer 21a are transmitted to the distal end portion of the probe 23 after passing a midway portion of the probe 23.

Further, a hand switch 21b that is capable of issuing an instruction for switching ultrasound vibrations on or off to the CPU 34 of the ultrasound driving power supply 3 in response to an operation of the surgeon or the like is provided in the grasping section 21.

A fluid feeding conduit 22a for supplying physiological saline from the irrigation unit 5 to the treatment target region 101 is provided inside the sheath 22. Further, (one part of) the proximal end portion and the midway portion of the probe 23 are inserted through the inside of the fluid feeding conduit 22a of the sheath 22.

A hollow part of the probe 23 is formed as a suction conduit 23a for sucking living tissue that has been crushed and emulsified by the action of ultrasound vibrations from the treatment target region 101. Further, an unshown conduit is provided in a linked manner with respect to the suction conduit 23a inside the grasping section 21. That is, living tissue that has been crushed and emulsified by the action of ultrasound vibrations is discharged to the waste water tank 7 after being sucked through the suction conduit 23a of the probe 23 and the unshown conduit provided inside the grasping section 21 accompanying operation of the pump 6.

As shown in FIG. 2, the ultrasound driving power supply 3 has an ultrasound oscillation section 31 that generates and outputs an ultrasound drive signal for driving the ultrasound transducer 21a that is equipped with a predetermined resonance frequency, a current/voltage detection section 32 that detects, at a predetermined frequency band, a magnitude of a current or a voltage of an ultrasound drive signal that is outputted from the ultrasound oscillation section 31, a filter processing section 33 that performs filter processing on a detection result obtained by the current/voltage detection section 32, a CPU 34 that is equipped with a function as a control section, a memory 34a, and an interface section 35. Further, a foot switch 36 that is capable of issuing an instruction for switching ultrasound vibrations on or off to the CPU 34 in response to an operation of a foot of the surgeon or the like is connected to the ultrasound driving power supply 3.

Figure 3:
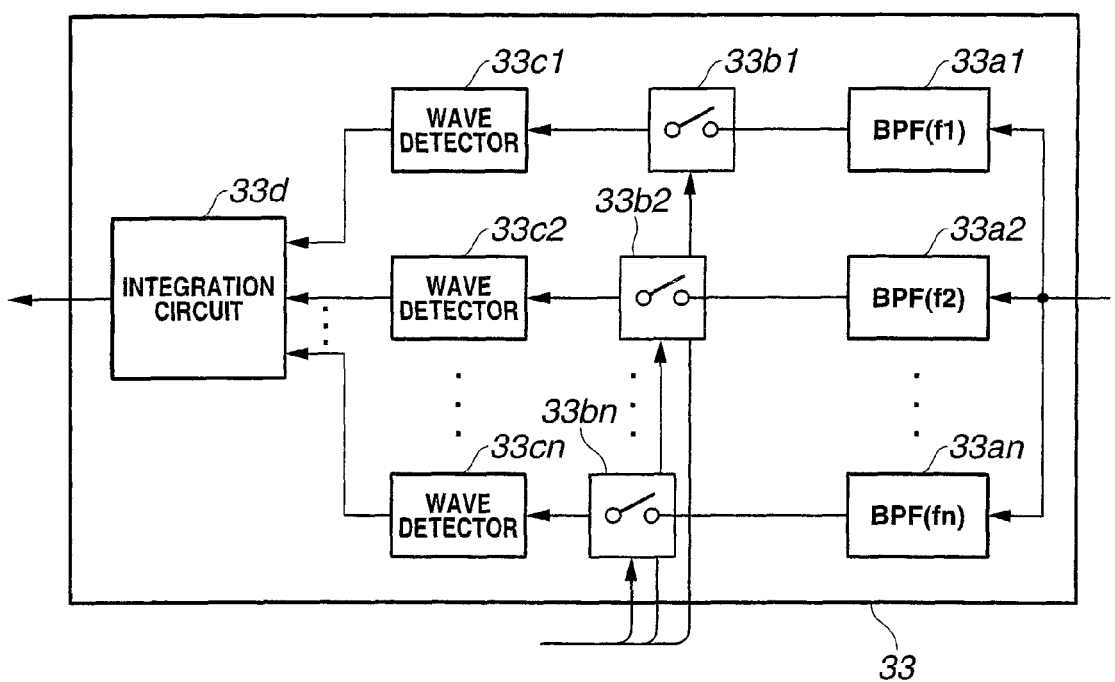
FIG. 3 is a block diagram that shows an example of the specific configuration of a filter processing section shown in FIG. 2.

As shown in FIG. 3, the filter processing section 33 includes n bandpass filters (in FIG. 3, abbreviated as "BPF") 33a1, 33a2, . . . , 33an into which a detection result from the current/voltage detection section 32 is inputted, respectively; n switches 33b1, 33b2, . . . , 33bn that are connected one-to-one with a post stage of the n bandpass filters; n wave detectors 33c1, 33c2, . . . , 33cn that are connected one-to-one with a post stage of each of the n switches; and an integrator 33d into which output signals from the n wave detectors are inputted.

The bandpass filters 33a1, 33a2, . . . , 33an are, for example, configured as filters in which parts (ends) of the passing frequency bands mutually overlap and in which center frequencies of the passing frequency bands are respectively different. In this connection, in FIG. 3, the center frequencies of the passing frequency bands of the bandpass filters 33a1, 33a2, . . . , 33an are denoted as f1, f2, . . . , fn (provided, it is assumed that f1<f2< . . . <fn).

The switches 33b1, 33b2, . . . , 33bn are switched on or off by the CPU 34 performing control based on a switching instruction of a filter switching switch 39 provided in the interface section 35. In this connection, a configuration may also be adopted such that the switches 33b1, 33b2, . . . , 33bn are switched on or off directly in response to a switching instruction from the filter switching switch 39.

Frequency components that pass through the switches 33b1, 33b2, . . . , 33bn that are in an "on" state are detected by the wave detectors 33c1, 33c2, . . . , 33cn, respectively, and thereafter subjected to integration processing by the integrator 33d.

The integrator 33d outputs a processing result of the aforementioned integration processing as a cavitation detection signal to the CPU 34. In this connection, the filter processing section 33 of the present embodiment may be configured using an accumulator instead of the integrator 33d. Further, in the present embodiment, the aforementioned integration processing may be performed by the CPU 34 instead of the integrator 33d.

The CPU 34 appropriately controls the operations of the irrigation unit 5 and the pump 6 as required based on a cavitation detection signal that is outputted from the filter processing section 33 and a switched state of each switch of a treatment speed switching section 38 provided in the interface section 35.

In this case, setting data that shows a correlation between switches that are switched on at the treatment speed switching section 38 and an appropriate cavitation generation state corresponding to the switches is previously stored in the memory 34a.

More specifically, when a switch (a switch 38a described later) that sets a treatment speed to a low speed is switched on at the treatment speed switching section 38, setting data that sets the generation state of cavitations to a first level is stored in the memory 34a. Further, when a switch (a switch 38b described later) that sets a treatment speed to a medium speed is switched on at the treatment speed switching section 38, setting data that sets the generation state of cavitations to a second level is stored in the memory 34a. Furthermore, when a switch (a switch 38c described later) that sets a treatment speed to a high speed is switched on at the treatment speed switching section 38, setting data that sets the generation state of cavitations to a third level is stored in the memory 34a. In this connection, it is assumed that a relationship is established between each of these kinds of setting data whereby the first level<second level<third level so that the amount of cavitations generated increases accompanying an increase in the treatment speed.

With respect to setting data that sets the generation state of cavitations to the first level, for example, a setting is made that makes the irrigation unit 5 operate normally or at a low output that has a lower load than at normal operation and also makes the pump 6 operate at a high output that has a greater load than at normal operation. Further, with respect to setting data that sets the generation state of cavitations to the second level, for example, a setting is made that causes both the irrigation unit 5 and the pump 6 to operate normally. Furthermore, with respect to setting data that sets the generation state of cavitations to the third level, for example, a setting is made that makes the irrigation unit 5 operate at a high output that has a greater load than at normal operation and also makes the pump 6 operate normally or at a low output that has a lower load than at normal operation.

More specifically, the CPU 34 previously reads in (for example, immediately after the power of the ultrasound driving power supply 3 is turned on) the respective setting data that are stored in the memory 34a, and appropriately performs operational control with respect to the irrigation unit 5 and the pump 6 based on a cavitation detection signal that is outputted from the filter processing section 33 and a switched state of each switch of the treatment speed switching section 38 provided in the interface section 35 while referring to the respective setting data that are read from the memory 34a.

Based on the switched state of each switch of the treatment speed switching section 38 provided in the interface section 35, the CPU 34 outputs a first display control signal for changing a display state of an indicator 37a provided in the interface section 35.

Based on a cavitation detection signal that is outputted from the filter processing section 33, as necessary the CPU 34 outputs a second display control signal for changing a display state of an indicator 37b provided in the interface section 35.

Based on a switched state corresponding to an instruction from the hand switch 21b and/or the foot switch 36, the CPU 34 performs control for switching on or off the operating state of the ultrasound oscillation section 31 that is equipped with a function as a drive section.

Based on a switching instruction of the filter switching switch 39 provided in the interface section 35, the CPU 34 performs control for switching the switches 33b1, 33b2, ..., 33bn of the filter processing section 33 on or off, respectively.

As shown in FIG. 4, the interface section 35 has an information presentation section 37 that visually shows information relating to a setting value and a measurement value of a cavitation generation state; the treatment speed switching section 38 that is capable of switching a treatment speed with respect to the treatment target region 101 in accordance with an operation of the surgeon or the like; and the filter switching switch 39 that is capable of switching a filter to be used in filter processing of the filter processing section 33 in accordance with an operation of the surgeon or the like. Each section of the interface section 35 described above is provided, for example, on a front panel of the ultrasound driving power supply 3.

The information presentation section 37 includes the indicator 37a that visually shows a setting value of a cavitation generation state and the indicator 37b that visually shows a measurement value of a cavitation generation state.

The treatment speed switching section 38 includes the switch 38a that is capable of issuing an instruction to set a treatment speed with respect to the treatment target region 101 to a low speed, the switch 38b that is capable of issuing an instruction to set a treatment speed with respect to the treatment target region 101 to a medium speed, and the switch 38c that is capable of issuing an instruction to set a treatment speed with respect to the treatment target region 101 to a high speed.

The indicator 37a changes its own display state in accordance with an output state of the first display control signal from the CPU 34. More specifically, when the switch 38a is turned on, for example (as shown in FIG. 4), the indicator 37a enters a display state in which a portion corresponding to "0" to "low speed" in a display area from a "0" graduation on a left end to a "Max" graduation on a right end is colored uniformly or substantially uniformly. Further, when the switch 38b is turned on, for example, the indicator 37a enters a display state in which a portion corresponding to "0" to "medium speed" in the display area from the "0" graduation on the left end to the "Max" graduation on the right end is colored uniformly or substantially uniformly. Furthermore, when the switch 38c is turned on, for example, the indicator 37a enters a display state in which a portion corresponding to "0" to "high speed" in the display area from the "0" graduation on the left end to the "Max" graduation on the right end is colored uniformly or substantially uniformly.

The indicator 37b changes its own display state in real time in accordance with an output state of the second display control signal from the CPU 34. More specifically, the indicator 37b enters a display state in which a portion from "0" to a part that corresponds to a level of the aforementioned cavitation detection signal in the display area from the "0" graduation on the left end to the "Max" graduation on the right end is colored uniformly or substantially uniformly. For example, a display state of the indicator 37b when the second display control signal is outputted in a case when the level of the aforementioned cavitation detection signal corresponds to "low speed" is as shown in FIG. 4.

In this connection, the indicators 37a and 37b may be indicators that are displayed as images on an LCD panel, or may be configured using a luminescent member such as an LED. (When the indicators 37a and 37b are configured using a luminescent member such as an LED, information relating to a setting value and a measurement value of a cavitation generation state can be displayed by means of the presence or absence of lighting instead of the presence or absence of coloring.)

The irrigation unit 5 supplies physiological saline that is sucked up from the water supply tank 4 to the treatment target region 101 via the ultrasound treatment handpiece 2. More specifically, the irrigation unit 5 that is equipped with a function as a fluid feeding section operates so as to increase an amount of fluid at the treatment target region 101.

The pump 6 sucks fluid that is retained at the treatment target region 101, that is fluid including living tissue and the like in a crushed and emulsified sate, via the ultrasound treatment handpiece 2, and thereafter discharges the sucked fluid to the waste water tank 7. More specifically, the pump 6 that is equipped with a function as a fluid suction section operates so as to reduce the amount of fluid at the treatment target region 101.

Operations of the operation system 1 of the present embodiment will now be described.

First, while grasping the grasping section 21, a surgeon performs an operation to bring the distal end portion of the probe 23 close to the treatment target region 101. Further, by switching the hand switch 21b or the foot switch 36 from "off" to "on" before or after the aforementioned operation, the surgeon starts the generation of ultrasound vibrations at the distal end portion of the probe 23. In this connection, the following description is based on an assumption that treatment is being performed in a state in which an output level of ultrasound vibrations at the distal end portion of the probe 23 (output level of an ultrasound drive signal that is outputted from the ultrasound oscillation section 31) is maintained at a fixed level.

Next, the surgeon starts operation of the irrigation unit 5 and the pump 6 while the distal end portion of the probe 23 that is generating ultrasound vibrations is still close to or in contact with the treatment target region 101. Further, for example, in order to set a treatment speed with respect to the treatment target region 101, the surgeon switches any single switch among the switches provided in the treatment speed switching section 38 from "off" to "on".

Upon the operations described above being performed, generation of cavitations begins at the treatment target region 101, and treatment involving crushing, emulsifying and sucking of living tissue of the treatment target region 101 starts.

Figure 5:
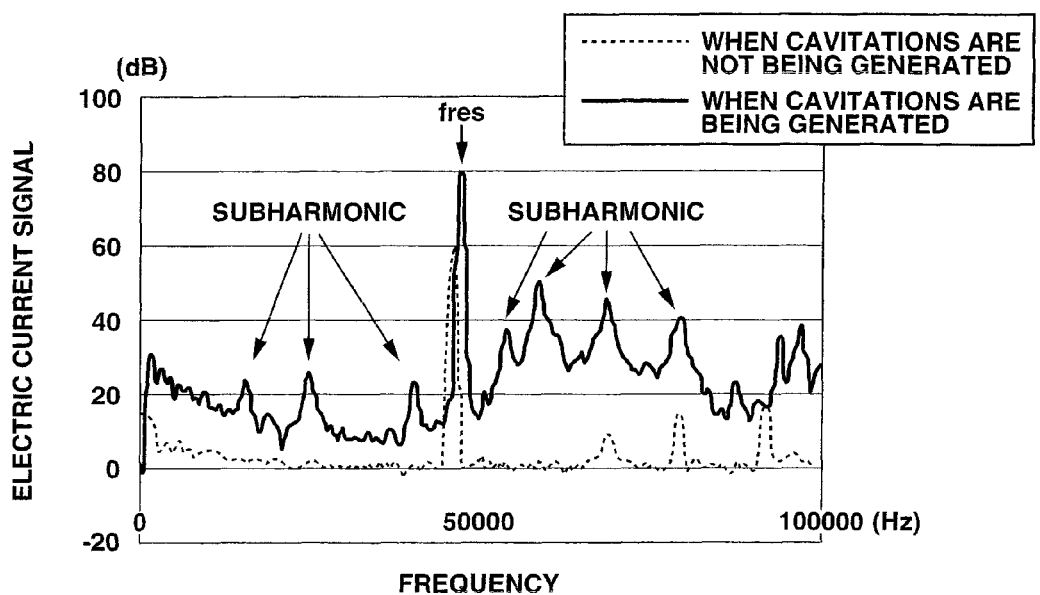
FIG. 5 is a view that shows an example of a detection result at a current/voltage detection section shown in FIG. 2.

Meanwhile, the current/voltage detection section 32 detects a magnitude of a current of an ultrasound drive signal that is outputted from the ultrasound oscillation section 31, for example, as a detection result illustrated in FIG. 5.

FIG. 5 is a view that shows detection results for magnitudes of a current of an ultrasound drive signal at the current/voltage detection section 32 as a frequency spectrum distribution. In this connection, in FIG. 5, a resonance frequency fres is set as 47 kHz. Further, in FIG. 5, (for comparison) a frequency spectrum distribution when cavitations are not being generated is shown by a broken line, and a frequency spectrum distribution when cavitations are being generated is shown by a solid line.

According to the detection results for magnitudes of a current exemplified in FIG. 5, the largest peak is detected at the resonance frequency fres, regardless of whether or not cavitations are generated.

Further, according to the detection results for the magnitudes of a current exemplified in FIG. 5, when cavitations are being generated, a number of noticeable peaks are detected at frequency components other than the resonance frequency fres, and when cavitations are not being generated, noticeable peaks are not detected at frequency components other than the resonance frequency fres.

Specifically, as shown in FIG. 5, when cavitations are being generated, a level of subharmonics corresponding to frequencies of divisors such as ½ or ¼ of the resonance frequency fres or of differences of these divisors becomes particularly higher in comparison to when cavitations are not being generated, and a level of frequency components other than the subharmonics also becomes higher in a substantially uniform manner. Therefore, a generation state of cavitations at the treatment target region 101 can be detected by detecting a signal level of a frequency band excluding a vicinity of the resonance frequency fres in the detection result for magnitudes of a current of an ultrasound drive signal at the current/voltage detection section 32.

In this connection, in the operation system 1 of the present embodiment, a detection result for magnitudes of a current of an ultrasound drive signal and a detection result for magnitudes of a voltage of the ultrasound drive signal exhibit substantially the same trends as each other. Therefore, even when a detection result for magnitudes of a voltage of the ultrasound drive signal are used instead of a detection result for magnitudes of a current of the ultrasound drive signal, the processing and operations described below can be performed in substantially the same manner.

Figure 6:
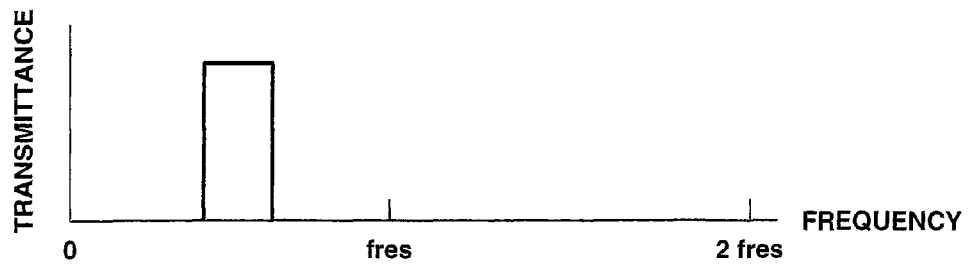
FIG. 6 is a view that shows an example of a passing frequency band in the filter processing section shown in FIG. 2.
Figure 7:
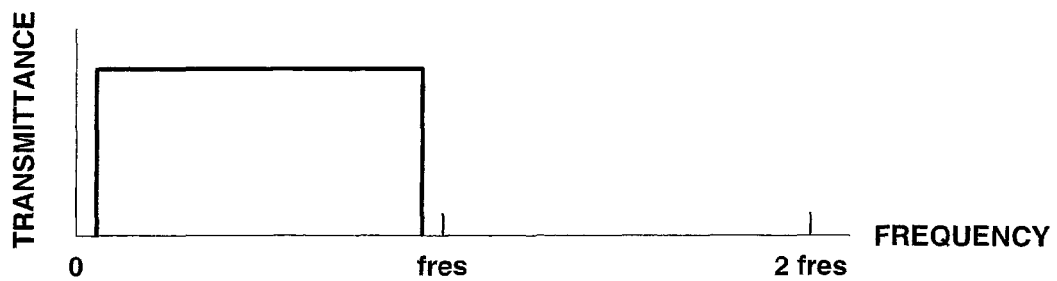
FIG. 7 is a view that shows an example of a passing frequency band in the filter processing section shown in FIG. 2, that is different to the example shown in FIG. 6.
Figure 8:
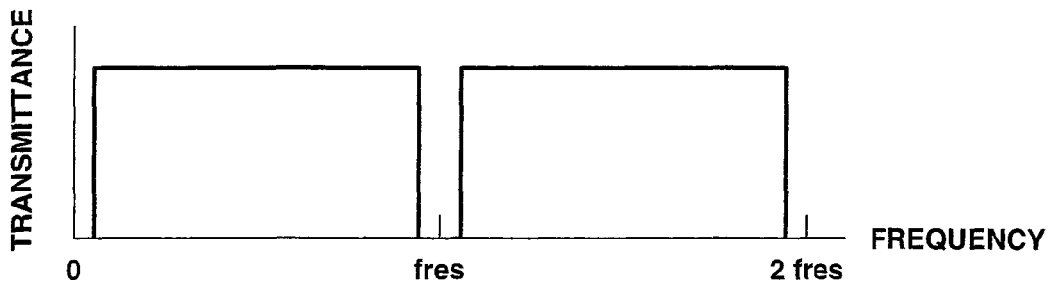
FIG. 8 is a view that shows an example of a passing frequency band in the filter processing section shown in FIG. 2, that is different to the examples shown in FIG. 6 and FIG. 7.

Based on control of the CPU 34, the filter processing section 33 switches the switches 33b1, 33b2, ..., 33bn, respectively, so that a passing frequency band in the bandpass filters 33a1, 33a2, ..., 33an becomes, for example, any one of the frequency bands shown in FIG. 6, FIG. 7, and FIG. 8.

FIG. 6 is a view that illustrates a case in which a passing frequency band at the bandpass filters 33a1, 33a2, ..., 33an is set so as to form a frequency band at one part on a low frequency side. More specifically, FIG. 6 illustrates a case in which a passing frequency band at the bandpass filters 33a1, 33a2, ..., 33an is set so as to form a frequency band that includes a subharmonic (divisor) of ½ of the resonance frequency fres.

FIG. 7 is a view that illustrates a case in which a passing frequency band at the bandpass filters 33a1, 33a2, ..., 33an is set from a frequency that is approximately 5% of the resonance frequency fres to a frequency that is 5% lower than the resonance frequency fres (i.e. a frequency that is 95% of the resonance frequency fres).

FIG. 8 is a view that illustrates a case in which passing frequency bands at the bandpass filters 33a1, 33a2, ..., 33an are set to the frequency band shown in FIG. 7 and also to a frequency band from a frequency that is 5% higher than the resonance frequency fres to a frequency that is 5% lower than a frequency (2 fres) of the second harmonic of the resonance frequency fres.

More specifically, a passing frequency band at the bandpass filters 33a1, 33a2, ..., 33an is set so as to exclude the resonance frequency of the ultrasound transducer 21a and to include at least a subharmonic of the resonance frequency.

The filter processing section 33 detects frequency components that pass the switches 33b1, 33b2, ..., 33bn that are in an "on" state at the wave detectors 33c1, 33c2, ..., 33cn, respectively, and after performing integration processing at the integrator 33d, the filter processing section 33 outputs the result of the integration processing as a cavitation detection signal to the CPU 34.

According to the detection result for magnitudes of a current exemplified in FIG. 5, there is a trend that shows that as a generation amount of cavitations increases, the aforementioned level of subharmonics becomes higher. Therefore, under a condition that a passing frequency band is the same at the bandpass filters 33a1, 33a2, ..., 33an, the result of integration processing at the integrator 33d is a value that increases relatively accompanying an increase in a cavitation generation amount, and that decreases relatively accompanying a decrease in a cavitation generation amount. More specifically, the CPU 34 of the present embodiment performs processing and operations as described hereafter by detecting such fluctuations in the aforementioned value as fluctuations in the level of a cavitation detection signal.

Upon detecting that the switch 38c has been switched on, the CPU 34 sets the generation state of cavitations to the aforementioned third level. The CPU 34 then performs control to cause the irrigation unit 5 to operate at a high output that has a greater load than at normal operation and also cause the pump 6 to operate normally or at a low output that has a lower load than at normal operation so that a level of a cavitation detection signal that is outputted from the filter processing section 33 reaches and is maintained at the aforementioned third level. According to this control, because an amount of fluid that is retained at the treatment target region 101 increases relatively, a generation amount of cavitations at the treatment target region 101 also increases relatively, and as a result a treatment speed with respect to the treatment target region 101 can be made a high speed.

Further, immediately after setting the cavitation generation state to the aforementioned third level, the CPU 34 outputs to the interface section 35 a first display control signal so as to cause a portion corresponding to an area from "0" to "high speed" of the indicator 37a to be colored uniformly or substantially uniformly. Further, while performing control to cause the level of the cavitation detection signal that is outputted from the filter processing section 33 to reach and be maintained at the aforementioned third level, as necessary the CPU 34 outputs a second display control signal to cause an area of the indicator 37b from "0" to a part corresponding to the level of the cavitation detection signal to be colored uniformly or substantially uniformly to the interface section 35. The display state of the indicator 37a thus enters a state that is in accordance with the first display control signal, and by the display state of the indicator 37b changing in real time in accordance with the second display control signal, a surgeon or the like can easily check whether or not the current cavitation generation state is a state that is suitable for a high-speed treatment speed.

Upon detecting that the switch 38a has been switched on, the CPU 34 sets a generation state of cavitations to the aforementioned first level. The CPU 34 then performs control to cause the irrigation unit 5 to operate normally or at a low output that has a lower load than at normal operation and also cause the pump 6 to operate at a high output that has a greater load than at normal operation so that a level of a cavitation detection signal that is outputted from the filter processing section 33 reaches and is maintained at the aforementioned first level. According to this control, because an amount of fluid that is retained at the treatment target region 101 decreases relatively, a generation amount of cavitations at the treatment target region 101 also decreases relatively, and as a result a treatment speed with respect to the treatment target region 101 can be made a low speed.

Further, immediately after setting the generation state of cavitations to the aforementioned first level, the CPU 34 outputs to the interface section 35 a first display control signal so as to cause a portion corresponding to an area from "0" to "low speed" of the indicator 37a to be colored uniformly or substantially uniformly. Further, while performing control to cause the level of the cavitation detection signal that is outputted from the filter processing section 33 to reach and be maintained at the aforementioned first level, as necessary the CPU 34 outputs the second display control signal to cause an area of the indicator 37b from "0" to a part corresponding to the level of the cavitation detection signal to be colored uniformly or substantially uniformly to the interface section 35. The display state of the indicator 37a thus enters a state that is in accordance with the first display control signal, and by the display state of the indicator 37b changing in real time in accordance with the second display control signal, a surgeon or the like can easily check whether or not the current cavitation generation state is a state that is suitable for a low-speed treatment speed.

As described in the foregoing, according to the operation system 1 of the present embodiment, a generation state (generation amount) of cavitations in the treatment target region 101 can be made an appropriate state that is in accordance with a treatment speed with respect to the treatment target region 101. Therefore, according to the operation system 1 of the present embodiment it is possible to stabilize the treatment capability of an apparatus that performs treatment with respect to the treatment target region 101 while utilizing cavitations (that are generated accompanying ultrasound vibrations) such as, for example, the ultrasound treatment handpiece 2.

Further, according to the operation system 1 of the present embodiment, it is possible to change a generation state (generation amount) of cavitations at the treatment target region 101 while maintaining an output level of ultrasound vibrations (output level of an ultrasound drive signal that is outputted from the ultrasound oscillation section 31) at the distal end portion of the probe 23 at a fixed level, that is, without particularly changing an amplitude of ultrasound vibrations at the ultrasound transducer 21a. Consequently, according to the operation system 1 of the present embodiment, a load that accompanies control with respect to the ultrasound transducer 21a can be reduced, and as a result the useful life of the ultrasound treatment handpiece 2 can be extended.

The present invention is not limited to the embodiment described above, and naturally various modifications and applications are possible within a range that does not depart from the spirit and scope of the invention.

What is claimed is:

1. An operation system, comprising:
an ultrasound transducer that is configured to generate ultrasound vibrations;
a drive section that drives the ultrasound transducer by means of a drive signal;
a probe that has a proximal end portion that is mechanically connected with the ultrasound transducer, and a distal end portion that can be brought adjacent to or in contact with a treatment target region of a treatment subject, the probe being configured to transmit ultrasound vibrations generated at the ultrasound transducer from the proximal end portion to the distal end portion;
a physico-chemical parameter adjustment section that changes a physico-chemical parameter of the treatment target region;
a detection section that detects a physical quantity that changes due to cavitations that are generated at the treatment target region by ultrasound vibrations of the distal end portion, based on the drive signal that is supplied to the ultrasound transducer;
a treatment speed switching section that is configured to switch a treatment speed with respect to treatment target region; and
a control section that controls a generation amount of cavitations at the treatment target region to be larger than the predetermined amount when the treatment speed set by the treatment speed switching section is faster than a predetermined speed, and causes a generation amount of cavitations at the treatment target region to be smaller than the predetermined amount when the treatment speed switching section is slower than the predetermined speed, by controlling the physico-chemical parameter adjustment section based on a detection result of the detection section.

2. The operation system according to claim 1, wherein:
the detection section detects as the physical quantity a magnitude of a current or a voltage at respective frequencies excluding a resonance frequency of the ultrasound transducer and including at least a subharmonic of the resonance frequency; and
the control section changes or maintains a generation state of cavitations at the treatment target region by controlling the physico-chemical parameter adjustment section based on a detection result of the detection section.

3. The operation system according to claim 1, further comprising:
an indicator that is configured to present a generation state of cavitations at the treatment target region as visual information;
wherein, the control section changes the visual information that is presented by the indicator as necessary to present visual information that is in accordance with the physical quantity that is detected at the detection section.

4. The operation system according to claim 1, wherein:
the physico-chemical parameter is an amount of fluid at the treatment target region; and
the physico-chemical parameter adjustment section comprises a fluid feeding section for supplying a fluid to the treatment target region.

5. The operation system according to claim 1, wherein:
the physico-chemical parameter is an amount of fluid at the treatment target region; and
the physico-chemical parameter adjustment section comprises a fluid suction section for sucking a fluid from the treatment target region.

6. The operation system according to claim 1, wherein:
the physico-chemical parameter is an amount of fluid at the treatment target region; and
the physico-chemical parameter adjustment section comprises a fluid feeding section for supplying a fluid to the treatment target region, and a fluid suction section for sucking a fluid from the treatment target region.

* * * * *

UNITED STATES PATENT AND TRADEMARK OFFICE
CERTIFICATE OF CORRECTION

PATENT NO. : 8,574,175 B2
APPLICATION NO. : 13/418555
DATED : November 5, 2013
INVENTOR(S) : Norihiro Yamada It is certified that error appears in the above-identified patent and that said Letters Patent is hereby corrected as shown below:

In the Claims

Column 10, line 13 (claim 1) should read: a control section that causes a generation amount of
cavi- Column 10, line 30 (claim 2) should read: the control section changes or maintains a generation
amount Signed and Sealed this
Twenty-second Day of April, 2014

Michelle K. Lee
*Deputy Director of the United States Patent and Trademark Office*